United States Patent [19]

Takashima et al.

[11] 4,210,660
[45] Jul. 1, 1980

[54] BENZAMIDE DERIVATIVES

[75] Inventors: Mutsuo Takashima, Kawagoe; Sumio Iwanami, Omiya; Shinji Usuda, Okegawa, all of Japan

[73] Assignee: Yamanouchi Pharmaceutical Co., Ltd., Tokyo, Japan

[21] Appl. No.: 971,504

[22] Filed: Dec. 20, 1978

[51] Int. Cl.$^2$ .................... C07D 207/14; A61K 31/40
[52] U.S. Cl. ................................. 424/274; 260/326.47
[58] Field of Search ..................... 260/326.47; 424/274

[56] References Cited

U.S. PATENT DOCUMENTS

| | | | |
|---|---|---|---|
| 3,342,826 | 9/1967 | Miller et al. | 260/326.47 |
| 3,862,139 | 1/1975 | Podesva et al. | 260/326.47 |
| 3,891,671 | 6/1975 | Thominet | 260/326.47 |
| 4,021,567 | 5/1977 | Kaplan et al. | 260/326.47 |
| 4,029,673 | 6/1977 | Bulteau et al. | 260/326.47 |

OTHER PUBLICATIONS

Murakami et al; Chem. Abs. vol. 86:72235d (1977) [Abstract of German Offen. 2,613,420].

Primary Examiner—Mary C. Lee
Attorney, Agent, or Firm—Burgess, Ryan and Wayne

[57] ABSTRACT

Benzamide derivatives represented by the formula

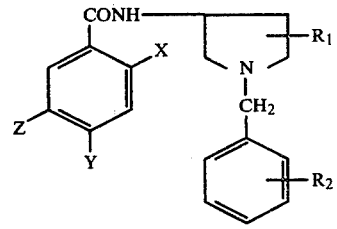

wherein X represents a lower alkoxy group; Y represents a mono- or di-lower alkylamino group; Z represents a halogen atom; $R_1$ represents a lower alkyl group; and $R_2$ represents a hydrogen atom or a halogen atom, and their pharmacologically acceptable nontoxic salts, which are strong central nervous system depressants, in particular strong antipsychotics.

6 Claims, No Drawings

BENZAMIDE DERIVATIVES

DETAILED DESCRIPTION OF THE INVENTION:

The present invention relates to novel benzamide derivatives and more particularly, relates to the benzamide derivatives represented by the formula III

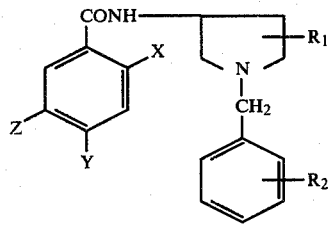

wherein X represents a lower alkoxy group; Y represents a mono- or di-lower alkylamino group; Z represents a halogen atom; $R_1$ represents a lower alkyl group; and $R_2$ represents a hydrogen atom or a halogen atom, and their pharmacologically acceptable nontoxic salts.

The compounds of formula III of this invention are novel and possess a very strong central nervous system (CNS) depressant activity, in particularly, a very strong antipsychotic activity and thus are expected to be useful compounds as strong CNS depressants, in particular, strong antipsychotics.

The terminology used in this specification and claims is as follows: The term "lower alkyl group" means a straight or branched chain alkyl group having 1–6 carbon atoms and includes, for example, a methyl group, ethyl group, propyl group, isopropyl group, n-butyl group, isobutyl group, sec-butyl group, tert-butyl group, amyl group, isoamyl group, and n-hexyl group. The term "lower alkoxy group" means a straight or branched chain alkoxy group having 1–6 atoms and includes, for example, a methoxy group, ethoxy group, propoxy group, isopropoxy group, n-butoxy group, amyloxy group, n-hexyloxy group, etc. Also, the term "halogen atom" includes a fluorine atom, chlorine atom, bromine atom, and iodine atom.

The compounds of this invention have one or two asymmetric carbon atom in the pyrrolidine ring, so that there exist stereoisomers such as optical isomers. The present invention also relates to these isomers.

Typical examples of the preferred compounds of this invention are illustrated below:
  N-(1-Benzyl-2-methyl-3-pyrrolidinyl)-5-chloro-2-methoxy-4-methylaminobenzamide;
  N-(1-Benzyl-2-methyl-3-pyrrolidinyl)-5-chloro-4-dimethylamino-2-methoxybenzamide;
  N-(1-Benzyl-4-methyl-3-pyrrolidinyl)-5-chloro-2-methoxy-4-methylaminobenzamide;
  N-(1-Benzyl-5-methyl-3-pyrrolidinyl)-5-chloro-2-methoxy-4-methylaminobenzamide;
  N-(1-Benzyl-3-methyl-3-pyrrolidinyl)-5-chloro-2-methoxy-4-methylamino-2-methoxybenzamide;
  N-(1-chlorophenylmethyl-3-methyl-3-pyrrolidinyl)-5-chloro-2-methyl-4-methylamino-2-methoxybenzamide;

The pharmacologically acceptable nontoxic salts of the compounds of this invention shown by formula III include the acid-addition salts thereof with an inorganic acid such as hydrochloric acid, hydrobromic acid, sulfuric acid, nitric acid, phosphoric acid, or an organic acid such as citric acid, acetic acid, lactic acid, tartaric acid, succinic acid, fumaric acid, maleic acid, etc., and the quaternary ammonium salts obtained by the reaction thereof and methyl iodide, ethyl iodide, methyl bromide, benzyl bromide, dimethylsulfate, methyl p-toluenesulfate, methanesulfonic acid, etc.

Hitherto, various compounds are known as the compounds possessing CNS depressant activity, in particular, antipsychotic activity and among these compounds, chlorpromazine is well-known and commercially available. However, the activity of chlorpromazine is yet insufficient and hence the discovery of medicaments possessing more excellent antipsychotic activity has been desired.

Since the compounds of this invention shown by formula III possess strong activities of reducing the conditioned avoidance response, and the apomorphine-induced stereotyped behavior, they show a very strong CNS depressant activity, in particular, antipsychotic activity. That is, the compounds of this invention shown by formula III are very strong CNS depressants, in particular, antipsychotics. Still further, the compounds of this invention shown by formula III also have a strong vasodilating action.

Now, Dutch Pat. No. 7,304,557 discloses that the N-(1-substituted-3-pyrrolidinyl) benzamide and thiobenzamide shown by the general formula

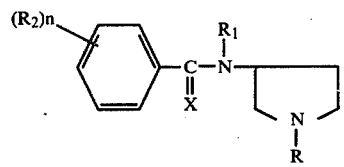

(wherein R represents a cycloalkyl group, a phenyl group, or a phenyl lower alkyl group; $R_1$ represents a hydrogen atom, a lower alkyl group having 1–8 carbon atoms, or a phenyl group; $R_2$ represents a halogen atom, a lower alkyl group, a lower alkoxy group, an amino group, a nitro group, a monoalkylamino group, a dialkylamino group, a mercaptomethyl group, an acetamide group, a sulfamoyl group, a cyano group, a hydroxy group, a benzyloxy group, or a trifluoromethyl group; X represents an oxygen atom or a sulfur atom; and n represents an integer of 0–3), have a strong antiemetic activity.

Also, as a compound having antipsychotic activity, sulpiride shown by the formula

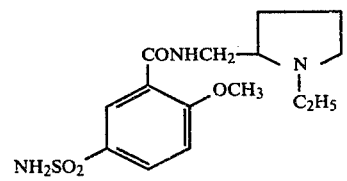

(Japanese Patent Publication No. 23,496/'69), and sultopiride shown by the formula

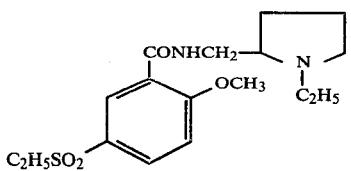

(Japanese Patent Publication No. 23,496/'69) are known. However, the compounds of this invention shown by formula III have remarkably stronger antipsychotic activity as compared with these known compounds. In addition, other known structural similar compounds to those of this invention are described in German patent application Offenlegungsschrift 2,613,420 (or British patent 1,520,584 & Spanish patent 451,958 corresponding to the German patent application).

The compounds of this invention shown by formula III can be prepared by reacting benzoic acid shown by formula I

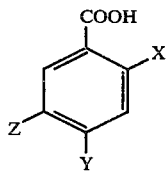

(wherein X, Y and Z have the same meanings as in formula III) or a reactive derivative thereof, with the amine shown by formula II

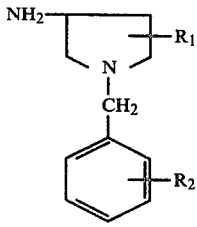

(wherein $R_1$ and $R_2$ have the same meaning as in formula III).

As the reactive derivatives of benzoic acid shown by formula I, there are illustrated an acid halide such as acid chloride, acid bromide, etc.; an acid azide; an ester such as methyl ester, ethyl ester, p-nitrophenyl ester, p-chlorophenyl ester, etc.; a symmetric acid anhydride; a mixed acid anhydride such as an alkyl carbonate mixed acid anhydride prepared by reacting the benzoic acid shown by formula I with an alkyl halocarbonate (e.g., methyl chlorocarbonate, ethyl chlorocarbonate, and ethyl bromocarbonate) and a mixed acid anhydride prepared by reacting the benzoic acid shown by formula I with an acid (e.g., alkylphosphoric acid, alkylphosphorous acid, and sulfuric acid) or the reactive derivatives thereof; and an active amide such as acid imidazolide or acid pyrrolidide prepared by reacting benzoic acid shown by formula I with N,N'-carbonyldiimidazole, N,N'-thionyldiimidazole, or N,N'-carbonyldipyrrole and an acid 2,4-dimethylpyrazolide prepared by reacting the acid hydrazide of the benzoic acid shown by formula I with acetylacetone.

The reaction of producing the compounds of this invention is practically carried out by condensing the benzoic acid shown by formula I or the reactive derivative thereof and an equimolar or excessive molar amount of the amine shown by formula II.

When the benzoic acid shown by formula I is a free carboxylic acid, the benzoic acid may be reacted with the amine of formula II at room temperature or under heating in an inert solvent in the presence of a condensing agent such as N,N'-dicyclohexylcarbodiimide, titanium tetrachloride, or a phosphorus halide (e.g., phosphorus trichloride, phosphorus oxychloride, diethyl chlorophoshite, o-phenylene chlorophosphite, and ethyl dichlorophosphite). Furthermore, the compounds of this invention may be also produced by reacting preliminarily the amine of formula II with the phosphorus halide in an inert solvent and then reacting the product thus obtained with the benzoic acid of formula I. For example, in the case of using phosphorus trichloride as the phosphorus halide, the amine of formula II is first reacted with about ½ mole of phosphorus trichloride in an inert solvent, under cooling, or at room temperature in the presence of a tertiary base such as triethylamine, pyridine, N,N-dimethylaniline, etc., and then reacting the product thus obtained with the benzoic acid of formula I in an inert solvent at room temperature or under heating, preferably under refluxing.

When an acid halide is used as the reactive derivative of the benzoic acid of formula I, the reaction is usually carried out in water under cooling or at room temperature in the presence of an alkali such as sodium hydroxide, potassium hydroxide, etc., or, in an inert solvent under cooling or at room temperature in the presence of a tertiary base such as triethylamine, pyridine, N,N-dimethylaniline, etc. When an acid azide is used as the reactive derivative of the benzoic acid of formula I, the reaction is usually carried out in water, under cooling, or at room temperature in the presence of an alkali such as sodium hydroxide, potassium hydroxide, etc. When an ester is used as the reactive derivate of the benzoic acid of formula I, the reaction is usually carried out in an inert solvent at room temperature or under heating, preferably under refluxing. When a symmetric acid anhydride or a mixed acid anhydride such as an alkyl carbonate mixed acid anhydride is used as the reactive derivative of the benzoic acid of formula I, the reaction is usually carried out in an inert solvent at room temperature or under heating in the presence of, if necessary, a tertiary base such as triethylamine, pyridine, N,N-dimethylaniline, etc. Also, when an active amide is used as the reactive derivative of the benzoic acid of formula I, the reaction is usually carried out in an inert solvent at room temperature or under heating. In addition, in these reactions, the reactive derivative of the benzoic acid of formula I may be reacted, if desired, with the amine of formula II without being isolated from the reaction mixture thereof.

The inert solvent used in the reaction of this invention is an inert organic solvent which does not participate to the reaction and preferred examples of such an inert organic solvent are benzene, toluene, xylene, methanol, ethanol, isopropanol, ether, dioxane, tetrahydrofuran, chloroform, dichloromethane, dichlorethane, etc. They may be properly selected according to the nature of the reactive derivative used.

The compounds of this invention shown by formula III thus prepared can be isolated and purified by an ordinary chemical operation such as extraction, recrystallization, column chromatography, etc.

In the following Experiment I, the compounds of this invention were compared with chlorpromazine which is a typical antipsychotic and other known structurally similar compounds in their activity in reducing apomorphine-induced stereotyped behavior.

Experiment I

According to the method of Janssen et al (Arzneim. Forsch., 15, 104 (1965), each of rats (male, Wistar, 200–250 g.) was placed in each observation cage, a test sample was administered subcutaneously to the rat, and after 30 minutes, 1.25 mg/kg of apomorphine was also administered intravenously to the rat. After a period of 5 minutes, 10 minutes, and 20 minutes, respectively, the symptom of apomorphine-induced stereotyped behavior was observed in each case. Then, from the relation of the ratio of inhibition and the amount of the test sample used, $ED_{50}$ was determined and the results are shown in Table I.

Table I

| Test sample | $ED_{50}$ (mg/Kg) |
| --- | --- |
| Known compound: | |
| Chlorpromazine | 2.5 |
| Sulpiride | >100 |
| Sultopiride | 18 |
| Compound of this invention: | |
| N-(1-Benzyl-2-methyl-3-pyrrolidinyl)-5-chlolo-2-methoxy-4-methylaminobenzamide [the compound of Example 3] | 0.01 |

It is clear from the results shown in the above table, that the compounds of this invention shown by formula III have a remarkably strong activity in reducing the apomorphine-induced stereotyped behavior by subcutaneous administration as compared with chlorpromazine which is a typical antipsychotic. It is also clear that the compounds of this invention had more strong CNS depressant activity, in particular antipsychotic activity, than these known compounds.

The compounds of this invention shown by formula III can be administered orally in the form of tablets, capsules, powder, syrup, etc., or can be administered parenterally by intramuscular injection, subcutaneous injection, intraveneous injection, or as a suppository, etc. The clinical dose of the compounds is 1–200 mg/day for adults in the case of oral administration and 1–150 mg/day for adult in the case of parenteral administration. The dosage may be properly changed according to the condition and age of a patient.

Reference Example 1

(a) To 80 ml of ethanol solution containing 16 g of 1-benzyl-2-methyl-3-pyrrolidone was added 80 ml of aqueous solution containing 13 g of hydroxylamine hydrochloride. After adding 18 g of sodium carbonate to the solution, the mixture was warmed to 35°–40° C. for 30 minutes. The reaction mixture was condensed under reduced pressure to half volume, and the product was extracted twice each time with 80 ml of ether. The extracts were combined and dried over anhydrous magnesium sulfate. The extracts were condensed under reduced pressure to provide 11 g of oily crude 1-benzyl-3-hydroxyimino-2-methylpyrrolidine.

Mass spectrum (m/e) 204 (M+)

(b) In 100 ml of methanol solution containing ammonia was suspended 11 g of crude 1-benzyl-3-hydroxyimino-2-methylpyrrolidine. About 2 g of Raney nickel was added to the suspension and 2 mole equivalents of hydrogen was absorbed in about 2 hours under room temperature and atmospheric pressure. The catalyst in the reaction mixture was removed by filtration and the reaction mixture was condensed. The residue thus obtained was distilled to provide 8 g of a colourless liquid of 3-amino-1-benzyl-2-methylpyrrolidine.

Boiling point (0.4 mmHg) 102°–103° C.

Mass spectrum (m/e) 190 (M+)

EXAMPLE 1

A solution of 30 ml of methylene chloride, 2.15 g of 5-chloro-2-methoxy-4-methylaminobenzoic acid and 1.12 g of triethylamine was cooled at $-10°$ C. to $-40°$ C. Subsequently, 1.2 g of ethyl chlorocarbonate was added dropwise with stirring and the reaction mixture was further stirred for 30 minutes at the same temperature. Then, 2.1 g of 3-amino-1-benzyl-2-methylpyrrolidine obtained in Reference Example 1 was added to the mixture at $-10°$ C. to $-40°$ C. followed by stirring for 30 minutes at the same temperature and further stirring for 2 hours at room temperature. The reaction mixture was washed with 20 ml of 1 N sodium hydroxide, water and 20 ml of 1 N hydrochloric acid respectively, and then dried over anhydrous magnesium sulfate. The solvent of the reaction mixture was distilled away and 10 ml of ether was added to the residue thus obtained to provide 3.1 g of colorless crystals of N-(1-benzyl-2-methylpyrrolidin-3-yl)-5-chloro-2-methoxy-4-methylaminobenzamide hydrochloride. The crystals were recrystallized from ethanol to provide colourless crystals having a melting point of 223°–228° C.

Elemental analysis for $C_{21}H_{26}N_3O_2Cl \cdot HCl$

| | C (%) | (%) | N (%) |
| --- | --- | --- | --- |
| Found: | 59.13 | 6.37 | 10.09 |
| Calculated: | 59.44 | 6.41 | 9.90 |

EXAMPLE 2

A solution of 15 ml of methylene chloride, 1.22 g of 5-chloro-4-dimethylamino-2-methoxybenzoic acid and 0.65 g of trimethylamine was cooled to $-10°$ C. to $-40°$ C. While stirring the solution, 0.6 g of ethyl chlorocarbonate was added dropwise followed by stirring for 30 minutes at the same temperature. Then, 1.05 g of 3-amino-1-benzyl-2-methylpyrrolidine obtained in Reference Example 1 was added to the mixture at $-10°$ C. to $-40°$ C. followed by stirring for 30 minutes at the same temperature and further for 2 hours at room temperature. The reaction mixture was washed with 10 ml of 1 N sodium hydroxide and water, respectively, and then the solvent of the reaction mixture was distilled away. The residue thus obtained was dissolved in a mixture of 5 ml of methanol and 2 ml of concentrated hydrochlorid acid followed by evaporation to dryness. The residue thus obtained was dissolved in 7 ml of isopropyl alcohol while heating and the solution was allowed to stand under cooling to provide 0.3 g of colorless needles of N-(1-benzyl-2-methylpyrrolidin-3-yl)-5-chloro-4-dimethylamino-2-methoxybenzamide hydrochloride (A) having a melting point of 222°–226° C. (decomposed). From the mother liquor, 0.2 g of N-(1-benzyl-2-methylpyrrolidin-3-yl)-5-chloro-4-dimethylamino-2-methoxybenzamide hydrochloride (B)

crystallized on further standing. Compounds (A) and (B) appeared to be stereoisomers each other from the value of nuclear magnetic resonance spectra.

Compound (A):

Elemental analysis for $C_{22}H_{28}N_3O_2Cl \cdot HCl \cdot H_2O$

|  | C (%) | H (%) | N (%) | Cl (%) |
|---|---|---|---|---|
| Found: | 57.71 | 6.70 | 9.10 | 15.74 |
| Calculated: | 57.90 | 6.85 | 9.21 | 15.54 |

Nuclear magnetic resonance spectrum ($d_6$-DMSO)
δ: 1.40 (methyl of pyrrolidine ring, d, 3H)

Compound (B)

Elemental analysis for $C_{22}H_{28}N_3O_2Cl \cdot HCl \cdot H_2O$

|  | C (%) | H (%) | N (%) | Cl (%) |
|---|---|---|---|---|
| Found: | 57.90 | 6.85 | 9.21 | 15.54 |
| Calculated: | 57.98 | 6.65 | 9.51 | 15.99 |

Nuclear magnetic resonance spectrum ($d_6$-DMSO)
δ: 1.36 (methyl of pyrrolidine ring, d, 3H)

In addition, in Mass spectra (m/e: 401, 403M+), both compounds (A) and (B) have the same fragmentation.

Reference Example 2

To a suspension of 4.88 g of fumaric acid in 26 ml of water was added dropwise 8.0 g of 3-amino-1-benzyl-2-methyl-pyrrolidine obtained in Reference Example 1(b) at 20°–30° C. with stirring. After further stirring for 1 hour under icecooling, crystals precipitated were recovered by filtration, and recrystallized from 15 ml of water. Colourless crystals obtained having a melting point of 182°–183° C. were converted to the free base in 8% aqueous sodium hydroxide solution followed by extracting the base with ether. The ether solution was concentrated to provide 2.0 g of 3-amino-1-benzyl-2-methylpyrrolidine (B).

Mass spectrum (m/e) 190 (M+)

(The product seemed to be the 2,3-cis isomer from the value of nuclear magnetic resonance spectrum.)

EXAMPLE 3

A solution of 1.53 g of 5-chloro-2-methoxy-4-methylaminobenzoic acid and 0.71 g of triethylamine in 30 ml of methylene chloride was cooled to −10° C.−−40° C. While stirring the solution, 0.7 g of ethyl chlorocarbonate was added dropwise followed by stirring for 30 minutes at the same temperature. Then, 1.4 g of 3-amino-1benzyl-2-methylpyrrolidine/(B) obtained in Reference Example 2 was added dropwise followed by stirring for 30 minutes at the same temperature and for 2 hours at room temperature. The reaction mixture was washed with water, with 20 ml of 1 N sodium hydroxide and further with water, and then dried over anhydrous magnesium sulfate. The solvent of the extract was distilled away, and 5 ml of ethyl acetate was added to the residue to provide 2.25 g of colourless crystals of N-(1-benzyl-2-methylpyrrolidin-3-yl)-5-chloro-2-methoxy-4-methylaminobenzamide.

By recrystallization from isopropanol, colourless crystals having a melting point of 152°–153° C. were obtained. (The product seemed to be the 2,3-cis isomer of pyrrolidine ring from the value of nuclear magnetic resonance spectrum.)

Elemental analysis for $C_{21}H_{26}N_3O_2Cl$

|  | C (%) | H (%) | N (%) | Cl (%) |
|---|---|---|---|---|
| Found: | 65.17 | 6.82 | 10.86 | 9.32 |
| Calculated: | 65.02 | 6.76 | 10.83 | 9.14 |

Reference Example 3

(a) To 210 ml of aqueous solution containing 2.5 g of hydroxylamine hydrochloride was added 210 ml of ethanol solution containing 25 g of 1-benzyl-5-methyl-3-pyrrolidone at about 15° C.

28 g of sodium carbonate was added, and the solution was stirred for 1 hour at the same tempereture. After the mixture was allowed to stand under icecooling overnight, 23 g of precipitated crude crystals of 1-benzyl-3-hydroxyimino-5-methylpyrrolidine having a melting point of 109°–110° C. was obtained.

Mass spectrum (m/e) 204 (M+)

(b) 23 g of crude crystals of crude 1-benzyl-3-hydroxyimino-5-methylpyrrolidine was suspended in 150 ml of methanol containing ammonia. Then, about 8 g of Raney nickel was added to the suspension, and 2 mole equivalents of hydrogen were absorbed under 50–60 atmospheric pressure at 18°–30° C. The catalyst was removed by filtration, and the solvent was distilled away. The residue obtained was distilled to provide 17.6 g of colorless liquid of 3-amino-1-benzyl-5-methyl-pyrrolidine.

Boiling point (2 mm Hg) 112°–115° C.

Mass spectrum (m/e) 190 (M+)

EXAMPLE 4

A solution of 1.53 g of 5-chloro-2-methoxy-4-methylaminobenzoic acid and 0.71 g of triethylamine in 30 ml of methylene chloride was cooled to −10°∼−40° C. To the solution was added dropwise 0.79 g of ethyl chlorocarbonate with stirring, and the mixture was stirred for 30 minutes at the same temperature. Then, 1.4 g of 3-amino-1-benzyl-5-methylpyrrolidine obtained in Reference Example 3 was added dropwise followed by stirring for 30 minutes at the same temperature, and then 2 hours at room temperature. The reaction mixture was washed with water, then with 20 ml of 1N sodium hydroxide, and further with water, and was dried over anhydrous magnesium sulfate.

The solvent was evaporated and the residue was converted to the hydrochloride in methanol, and the product was recrystalized from a mixture of isopropanol/methanol to provide 1.1 g of colorless crystals of N-(1-benzyl-5-methylpyrrolidin-3-yl)-5-chloror-2-methoxy-4-methylaminobenzamide hydrochloride. The product shows a melting point of 224°–226° C.

Elementary analysis for $C_{21}H_{26}N_3O_2Cl \cdot HCl$

|  | C (%) | H (%) | N (%) | Cl (%) |
|---|---|---|---|---|
| Found | 59.19 | 6.56 | 9.77 | 16.74 |
| Calculated | 59.44 | 6.41 | 9.90 | 16.71 |

Reference Example 4

In a mixture of 40 ml of isopropanol and 4 ml of water was suspended 5.95 g of fumaric acid, and to the suspension was added dropwise 9.5 g of 3-amino-1-benzyl-5-methylpyrrolidine at 20°–30° C. with stirring. After adding 60 ml of isopropanol to the solution, 4 g of the precipitated crystals were recovered by filtration. The crystals obtained were recrystalized from a mixture of 40 ml of methanol and 40 ml of isopropanol to provide 2.4 g of colorless needles having a melting point of 192°–193° C. The product was converted to the free base in 8% aqueous sodium hydroxide, and the base was extracted with ether. The extract was dried, and concentrated to provide 1.8 g of 3-amino-1-benzyl-5-methylpyrrolidine.

Mass spectrum (m/e) 190(M+)

(The product seemed to be either the 2,4-cis isomer or 2,4-trans isomer from the data of nuclear magnetic resonance spectrum ($^{13}$C) and gaschromatography.)

EXAMPLE 5

A solution of 1.53 g of 5-chloro-2-methoxy-4-methylaminobenzoic acid and 0.71 g of triethylamine in 30 ml of methylene chloride was cooled to −10°–−40° C. Subsequently, 0.79 g of ethyl chlorocarbonate was added dropwise to the solution followed by stirring for 30 minutes at the same temperature.

Then, 1.4 g of 3-amino-1-benzyl-5-methylpyrrolidine obtained in Reference Example 4 was added dropwise to the mixture followed by stirring for 30 minutes at the same temperature and further for 3 hours at room temperature. The reaction mixture was washed with 20 ml of 1 N sodium hydroxide and water, and then dried over anhydrous magnesium sulfate. The solvent of the reaction mixture was distilled away, and the residue obtained was treated with column chromatography [silica gel; chloroform(methanol 5%)] to provide 1.6 g of colourless solid of N-(1-benzyl-5-methylpyrrolidin-3-yl)-5-chloro-2-methoxy-4-methylaminobenzamide. The product was converted to the fumaric acid salt in methanol, and recrystallized from isopropanol to provide crystals having a melting point of 178°–179° C.

Elemental analysis for $C_{21}H_{26}N_3O_2Cl \cdot C_4H_4O_4$

|  | C (%) | H (%) | N (%) | Cl (%) |
| --- | --- | --- | --- | --- |
| Found | 59.44 | 5.96 | 8.50 | 7.19 |
| Calculated | 59.58 | 6.00 | 8.34 | 7.03 |

[The products of Example 4 and 5 seemed to be stereoisomers each other from the value of nuclear magnetic resonance spectra ($^{13}$C).]

Reference Example 5

(a) To an aqueous solution containing 50 g of hydroxylamine hydrochloride was added 200 ml of ehanol solution containing 26 g of 1-benzyl-4-methyl-3-pyrrolidone at 20°–25° C. After adding 40 g of sodium carbonate, the reaction mixture was stirred at room temperature overnight. After adding 100 ml of water, the mixture was extracted twice each time with 200 ml and 50 ml of methylene chloride. The extracts were combined and dried over anhydrous magnesium sulfate, and the solvent of the extract was distilled away. To the residue was added ethyl acetate to provide 26 g of crude crystals of 1-benzyl-3-hydroxyimino-4-methyl-pyrrolidine having a melting point of 97°–99° C.

Mass spectrum (m/e) 204(M+)

(b) 26 g of crude crystals of 1-benzyl-3-hydroxyimino-4 methylpyrrolidine were suspended in 150 ml of methanol solution containing ammonia. Then 8 g of Raney nickel was added to the suspension, and 2 mole equivalents of hydrogen was absorbed under 80–100 atmospheric pressure of hydrogen at 18°–30° C. The catalyst was removed by filtration, and the solvent was distilled away. The residue thus obtained was distilled to provide 18.5 g of colourless liquid of 3-amino-1-benzyl-4-methylpyrrolidine.

Boiling point (0.8 mmHg) 108°–110° C.

Mass spectrum (m/e) 190 (M+)

EXAMPLE 6

A solution of 1.53 g of 5-chloro-2-methoxy-4-methylamino-benzoic acid and 0.71 g of triethylamine in 30 ml of methylene chloride was cooled to −10°–−40° C. Subsequently, 0.79 g of ethyl chlorocarbonate was added dropwise with stirring to the solution and, the the solution was further stirred for 30 minutes at the same temperature. Then, 1.4 g of 3-amino-1-benzyl-4-methylpyrrolidine obtained in Reference Example 5 was added dropwise to the solution followed by stirring for 30 minutes at the same temperature and further 2 hours at room temperature. The reaction mixture was washed with water, 20 ml of 1 N sodium hydroxide and further with water respectively, and then dried over anhydrous magnesium sulfate. The solvent of the extract was distilled away, and 2.6 g of the residue was obtained. To 0.2 g of this residue (2.6 g) was added 2 ml of ether and 2 ml of hexane. After allowing to stand, 0.1 g of colourless crystals of N-(1-benzyl-4-methylpyrrolidin-3yl)-5-chloro-2-methoxy-4methylamino-benzamide were obtained. by recrystallization from a mixture of ether-hexane, crystals having a melting point of 73°–76° C. were obtained.

Elemental analysis for $C_{21}H_{26}N_3O_2Cl$

|  | C (%) | H (%) | N (%) |
| --- | --- | --- | --- |
| Found | 64.88 | 6.79 | 11.04 |
| Calculated | 65.02 | 6.76 | 10.83 |

Subsequently, 2.4 g of the aforementioned residue(2.6 g) was treated with column chromatography [silica gel; chloroform (methanol 2.5%)], and 0.8 g of oily N-(1-benzyl-4-methyl-pyrrolidin-3-yl)-5-chloro-2-methoxy-4-methylaminobenzamide (A) was obtained as a component of the first eluate. The product was converted to the hydrochloride in isopropanol, and recrystallized from a mixture of isopropanol-methanol to provide colourless crystals having a melting point of 234°–236° C. (decomp.).

Elemental analysis for $C_{21}H_{26}N_3O_2Cl \cdot HCl$

|  | C (%) | H (%) | N (%) |
| --- | --- | --- | --- |
| Found | 59.29 | 6.45 | 9.71 |
| Calculated | 59.44 | 6.41 | 9.90 |

Further, 1.0 g of N-(1-benzyl-4-methylpyrrolidin-3-yl)-5-chloro-2-methoxy-4-methylaminobenzamide (B) was obtained as a component of the second eluate. The product was recrystallized from a mixture of ethyl acetate-hexane to provide colourless crystals having a melting point of 89°–90° C.

Elemental analysis for $C_{21}H_{26}N_3O_2Cl$

|  | C (%) | H (%) | N (%) |
| --- | --- | --- | --- |
| Found | 65.13 | 6.76 | 10.75 |
| Calculated | 65.02 | 6.76 | 10.83 |

[The products (A) and (B) aforementioned seemed to be the 3,4-cis isomer and 3,4-trans isomer from the values of nuclear magnetic resonance spectra.]

What is claimed is:

1. Benzamide compounds of the formula

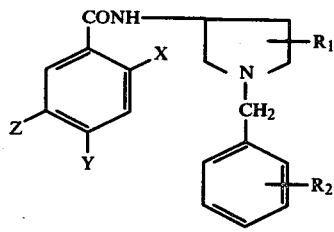

wherein X represents a lower alkoxy group, Y represents a mono- or di-lower alkyl amino group; Z represents a halogen atom; R₁ represents a lower alkyl group; and R₂ represents a hydrogen atom or halogen atom; and the pharmacologically acceptable nontoxic salts thereof.

2. N-(1-Benzyl-2-methyl-3-pyrrolidinyl)-5-chloro-2-methoxy-4-methylaminobenzamide and the pharmacologically acceptable non-toxic salts thereof as claimed in claim 1.

3. N-(1-Benzyl-2-methyl-3-pyrrolidinyl)-5-chloro-4-dimethylamino-2-methoxybenzamide and the pharmacologically acceptable non-toxic salts thereof as claimed in claim 1.

4. N-(1-Benzyl-5-methyl-3-pyrrolidinyl)-5-chloro-2-methoxy-4-methylaminobenzamide and the pharmacologically acceptable non-toxic salts thereof as claimed in claim 1.

5. N-(1-Benzyl-4-methyl-3-pyrrolidinyl)-5-chloro-2-methoxy-4-methylaminobenzamide and the pharmacologically acceptable non-toxic salts thereof as claimed in claim 1.

6. A pharmaceutical composition comprising a CNS depressing-effective amount of a benzamide compound of the formula

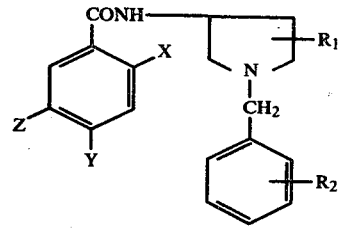

wherein
X is a lower alkoxy group,
Y is a mono- or di-lower alkyl amino group,
Z is a halogen atom,
R₁ is a lower-alkyl group and
R₂ is a hydrogen or a halogen atom or a non-toxic salt thereof and a pharmaceutically acceptable carrier.

* * * * *

UNITED STATES PATENT OFFICE
CERTIFICATE OF CORRECTION

Patent No. 4,210,660        Dated July 1, 1980

Inventor(s) Mutsuo Takashima, et al

It is certified that error appears in the above-identified patent and that said Letters Patent are hereby corrected as shown below:

Column 6, line 59: "hydrochlorid" should be --hydrochloride--.

Column 9, line 50: "ehanol" should be --ethanol--.

Signed and Sealed this

Tenth Day of March 1981

[SEAL]

Attest:

RENE D. TEGTMEYER

Attesting Officer    Acting Commissioner of Patents and Trademar